United States Patent [19]

Deckner et al.

[11] Patent Number: 5,824,666
[45] Date of Patent: *Oct. 20, 1998

[54] LOW PH, HYDROLYTICALLY STABLE, COSMETIC COMPOSITIONS CONTAINING ACIDIC ACTIVES

[75] Inventors: George Endel Deckner, Cincinnati; Marie Antoinette Rinaldi; Victoria Claire Szymanski, both of Maineville, all of Ohio

[73] Assignee: The Procter & Gamble Company, Cincinnati, Ohio

[ * ] Notice: The term of this patent shall not extend beyond the expiration date of Pat. No. 5,665,364.

[21] Appl. No.: 576,264

[22] Filed: Dec. 21, 1995

Related U.S. Application Data

[63] Continuation of Ser. No. 212,413, Mar. 11, 1994, abandoned.

[51] Int. Cl.$^6$ .............................. A61K 7/44; A61K 7/40; A61K 9/10; A01N 37/10
[52] U.S. Cl. ......................... 514/152; 514/153; 514/159; 514/165; 514/345; 514/569; 514/574; 514/576; 514/596; 514/649; 514/675; 514/717; 514/718; 514/725; 514/731; 514/847; 424/401; 252/312
[58] Field of Search .................................... 514/410, 152, 514/153, 159, 165, 346, 360, 847, 399, 345, 569, 574, 576, 596, 649, 675, 717, 718, 725, 731; 252/312, 309; 424/401

[56] References Cited

U.S. PATENT DOCUMENTS

| | | | |
|---|---|---|---|
| 3,355,387 | 11/1967 | Hinkel | 252/353 |
| 4,732,930 | 3/1988 | Tanaka et al. | 524/742 |
| 4,822,604 | 4/1989 | Knoll et al. | 514/160 |
| 5,051,251 | 9/1991 | Morita et al. | 424/70.28 |
| 5,073,372 | 12/1991 | Turner et al. | 424/401 |
| 5,229,104 | 7/1993 | Sottery et al. | 514/725 |
| 5,262,407 | 11/1993 | Leveque et al. | 514/159 |
| 5,482,710 | 1/1996 | Slavtcheff et al. | 424/195.1 |
| 5,484,597 | 1/1996 | Slavtcheff et al. | 424/401 |
| 5,618,522 | 4/1997 | Kaleta et al. | 514/59 |
| 5,652,522 | 7/1997 | Bisset | 514/77 |
| 5,665,364 | 9/1997 | McAtee et al. | 424/401 |

FOREIGN PATENT DOCUMENTS

| | | | |
|---|---|---|---|
| A2 202621 | 11/1986 | European Pat. Off. | A61K 7/06 |
| A2 347145 | 12/1989 | European Pat. Off. | A61K 9/26 |
| 92/13566 | 8/1992 | WIPO | A61K 47/32 |
| 92/19214 | 11/1992 | WIPO | A61K 7/00 |
| 94/02176 | 2/1994 | WIPO | A61K 47/32 |
| 95/03781 | 2/1995 | WIPO | A61K 7/48 |

OTHER PUBLICATIONS

Multi–phase Oil–in–Water Emulsions, Gillian M. Eccleston, J. Soc. Cosmet. Chem. 41, 1–22 (Jan./Feb. 1990).

Hydroxy Acids and Skin Aging, Walter P. Smith, Walter Smith Consultants, Soap/Cosmetics/Chemical Specialities for Sep., 1993.

New Oil–in–Water Concepts Based on Emulsifiers derived from Renewable Raw Materials, Gerd Dahms, ICI Surfactants, RP 58/91E (Feb. 1991).

Liquid Crystals in Cosmetics Emulsions, Dr. P. Loll, ICI Surfactants, RP 94–93E (Date unknown).

Properties of O/W Emulsions with Anisotropic Lamellar Phases, Gerd Dahms, Cosmetics & Toiletries, vol. 101, Nov. 1986.

*Primary Examiner*—Richard D. Lovering
*Assistant Examiner*—Daniel S. Metzmaier
*Attorney, Agent, or Firm*—Loretta J. Henderson

[57] ABSTRACT

The present invention relates to leave on, oil-in-water, skin care compositions, comprising: (A) from about 0.05% to about 20% of an acidic active ingredient, preferably having a solubility parameter from about 6 to about 12; (B) from about 0.1% to about 25% of alkoxylated alcohols, alkoxylated polyols, and mixtures thereof; (C) from about 1% to about 20% of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.; (D) from about 0.05% to about 10% of an acid stable, hydrophilic surfactant selected from the group consisting of anionic, cationic, zwitterionic, nonionic surfactant, and mixtures thereof; and (F) from about 25% to about 99.7% water; wherein the pH of the composition is about 3.5 or less. These cosmetic compositions provide improved physical and chemical stability, while providing good skin deposition and good skin penetration of the active ingredients, while also providing low dermal irritation.

24 Claims, No Drawings

LOW PH, HYDROLYTICALLY STABLE, COSMETIC COMPOSITIONS CONTAINING ACIDIC ACTIVES

This is a continuation of application Ser. No. 08/212,413, filed on Mar. 11, 1994, now abandoned.

TECHNICAL FIELD

The present invention relates to hydrolytically stable, low pH, leave-on skin care cosmetic compositions containing acidic actives such as salicylic acid. In particular it relates to stable, low pH, cosmetic compositions having liquid crystalline phases, providing improved moisturization and hydration as well as improved chemical and physical stability, while providing low dermal irritation.

BACKGROUND OF THE INVENTION

A wide variety of acidic active ingredients are currently known for treating various skin conditions. Unfortunately, it is more difficult to formulate these acidic actives into oil-in-water emulsions which are stable, due to in part to their acidic nature and their limited solubility characteristics. Representative of some of these active ingredients is salicylic acid.

Cosmetic compositions containing salicylic acid are known in the art, and help to increase skin cell turnover and ultimately provide younger, fresher, healthier looking skin. Salicylic acid is a well known keratoylic agent which is believed to help remove keratin plugs and to aid the skin's exfoliation process described hereinafter. Salicylic acid is also known for its anti-acne, anti-skin aging benefits, etc., described further in C. Huber et al., *Arch. Derm Res.* 257, pp. 293–297, 1977 which is herein incorporated by reference. See also PCT Patent Application No. 9310756, to Blank, published Jun. 10, 1993.

Skin is composed of two layers: the epidermis (or cuticle) and the dermis. The epidermis is a thin outer layer composed of stratified epithelium. The outermost layer of the epidermis is the stratum corneum which is composed of keratin, protein-filled, flattened cells surrounded by thin lipid layers. The cells are believed to be attached to one another by protein connections (desmosomes) between cells. The cells in the deepest portion of the epidermis, the basal layer, multiply and grow, pushing the older cells of the epidermis upward and toward the surface. As these cells move upward they become flattened. The epidermis is generally devoid of blood vessels and depends on blood vessels found in the dermis for nutrition. The more superficial cells of the epidermis, being far removed from the nutrient supply, gradually differentiate, transforming their proteins into keratin. This process of keratinization results in the death of the cells. Keratin is an insoluble proteinaceous material and gives the stratum corneum a horn-like consistency. The outermost dead stratum corneum cells are gradually shed and replaced by more recently keratinized cells.

It typically takes approximately thirty days for a cell to migrate from the basal layer of the epidermis to sloughing off and discarding at the outer layers of the stratum corneum. As the cell migrates outward from the basal layer, it progressively keratinizes until it is relatively impermeable. The result is the stratum corneum, an extremely thin surface layer (10 microns) with substantial barrier properties. The cell envelopes in the stratum corneum tend to be mainly polar lipids, such as ceramides, sterols, and fatty acids, while the cytoplasm of stratum corneum cells remains polar and aqueous.

In normal skin, the stratum corneum is shed as individual cells or as small clusters of cells. Skin problems such as dry skin, etc., are disorders of keratinization in which the shedding of stratum corneum cells at the skin surface is altered relative to normal, young, healthy skin. Such alteration results in large clusters of cells leading to visible scaling of the skin, a build-up of keratinaceous material on the skin surface or in follicles or ducts and/or a rough texture to the skin surface. These conditions may be improved by applying cosmetic compositions, i.e. containing salicylic acid, which can aid in the removal of the outermost keratinaceous material.

Although attempts have been made to partially neutralize these acidic actives to improve formulatibility and reduce irritation potential of the skin, this approach appears to decrease the skin penetration of the acidic active ingredients.

Therefore, efficacious cosmetic compositions which stabilize acidic actives such as salicylic acid, for removing surface scales from the stratum corneum, are needed.

Therefore, it is an object of the present invention to provide novel, low pH, oil-in-water emulsions containing acidic actives, these compositions being physically and chemically stable, while providing good skin deposition and good skin penetration of the active ingredient, while also providing low dermal irritation.

Therefore, it is an object of the present invention to provide novel compositions for enhancing skin moisturization and hydration by removal of dry skin cells or scales from the stratum corneum.

It is a further object of the present invention to provide such compositions with low dermal irritation, especially in compositions requiring a low pH.

It is a further object of the present invention to provide such compositions with low dermal irritation, especially in compositions requiring an acidic active.

It is still a further object of the present invention to provide such compositions having good stability of the acidic active components in a cosmetically elegant form.

SUMMARY OF THE INVENTION

The present invention relates to leave on skin care compositions comprising:

(A) from about 0.05% to about 20% of an acidic active ingredient, preferably having a solubility parameter from about 6 to about 12;

(B) from about 0.1% to about 25% of alkoxylated alcohols, alkoxylated polyols, and mixtures thereof, of the formula:

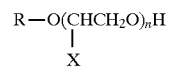

wherein R is selected from the group consisting of alcohols, polyols, diols, and mixtures thereof, having a chainlength of from about 2 to about 18 carbon atoms; n is an integer from about 3 to about 40; X is selected from the group consisting of hydrogen, methyl, ethyl, propyl, and mixtures thereof;

(C) from about 1% to about 20% of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;

(D) from about 0.05% to about 10% of an acid stable, hydrophilic surfactant selected from the group consisting of anionic, cationic, zwitterionic, nonionic surfactant, and mixtures thereof; and (F) from about 25% to about 99.7% water;

wherein the pH of the composition is about 3.5 or less, preferably from about 2.5 to about 3.5, more preferably from about 2.8 to about 3.2.

In further embodiments the present invention relates to leave on skin care compositions comprising:

(A) from about 0.1% to about 5% of salicylic acid;

(B) from about 0.1% to about 25% of alkoxylated alcohols, alkoxylated polyols, and mixtures thereof, of the formula:

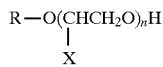

wherein R is selected from the group consisting of alcohols, polyols, diols, and mixtures thereof, having a chainlength of from about 2 to about 18 carbon atoms; n is an integer from about 3 to about 40; X is selected from the group consisting of hydrogen, methyl, ethyl, propyl, and mixtures thereof;

(C) from about 1% to about 20% of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;

(D) from about 0.05% to about 10% of an acid stable, hydrophilic surfactant selected from the group consisting of anionic, cationic, zwitterionic, nonionic surfactant, and mixtures thereof; and (F) from about 25% to about 99.7% water;

wherein the pH of the composition is about 3.5 or less, preferably from about 2.5 to about 3.5, more preferably from about 2.8 to about 3.2.

All percentages and ratios used herein are by weight of the total composition. All measurements made are at 25° C., unless otherwise designated. The invention hereof can comprise, consist of, or consist essentially of, the essential as well as optional ingredients and components described herein.

DETAILED DESCRIPTION OF THE INVENTION

The cosmetic compositions of the present invention are useful for moisturizing and hydrating the skin and for depositing acidic active ingredients onto the skin. These compositions are in the form of oil-in-water emulsions whereby the oil phase and the water phase can contain, in addition to the essential components described herein, a variety of ingredients known in the art. The acidic active ingredients are preferably deposited to the skin from the oil phase of the oil-in-water emulsion. The acidic active ingredients for use herein will therefore preferably have a solubility parameter from about 6 to about 12.

In particular the present invention relates to leave on skin care compositions which are oil-in-water emulsions, comprising:

(A) from about 0.05% to about 20% of an acidic active ingredient, preferably having a solubility parameter from about 6 to about 12;

(B) from about 0.1% to about 25% of alkoxylated alcohols, alkoxylated polyols, and mixtures thereof, of the formula:

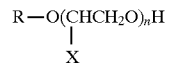

wherein R is selected from the group consisting of alcohols, polyols, diols, and mixtures thereof, having a chainlength of from about 2 to about 18 carbon atoms; n is an integer from about 3 to about 40; X is selected from the group consisting of hydrogen, methyl, ethyl, propyl, and mixtures thereof;

(C) from about 1% to about 20% of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;

(D) from about 0.05% to about 10% of an acid stable, hydrophilic surfactant selected from the group consisting of anionic, cationic, zwitterionic, nonionic surfactant, and mixtures thereof; and (F) from about 25% to about 99.7% water;

wherein the pH of the composition is about 3.5 or less, preferably from about 2.5 to about 3.5, more preferably from about 2.8 to about 3.2.

Preferably the ratio of component (C) to component (D) is from about 20:1 to about 1:1, preferably from about 10:1 to about 1:1, more preferably from about 5:1 to about 1:1, and even more preferably about 3:1. These ratios allow for the formation of a lamellar liquid crystalline phases, which contributes to the physical and chemical stability of the composition at temperatures from about −10° C. to about 50° C. at a pH of about 3.5 or less.

The compositions of the present invention have complex rheological characteristics. These compositions have physical properties characteristic of oil-in-water emulsions, liquid crystals, as well as crystalline gel networks.

The nature of liquid crystals, the formation of liquid crystals, the properties and advantages of liquid crystals are described further in G. Dahms, Properties of O/W Emulsions with Anisotropic Lamellar Phases, 101 *Cosmetics & Toiletries* 113–115, (1986); P. Loll, Liquid Crystals in Cosmetic Emulsions, *ICI Surfactants' Publication RP94-93E;* and G. M. Eccleston, Multiple-Phase Oil-In-Water Emulsion, 41 *J. Soc. Cosmet. Chem.* 1–22, (January/February 1990); all of which are incorporated herein by reference in their entirety.

The oil-in-water emulsions herein have desirable aesthetic and elegant properties, such as a rich and creamy, yet non-greasy, skin feel. These emulsions can span a broad range of consistencies from thin lotions to heavy creams. These emulsions typically have viscosities ranging from about 100 cps to about 500,000 cps, preferably from about 3,000 to about 200,000, more preferably from about 5000 cps to about 150,000 cps, and even more preferably from about 5000 cps to about 100,000 cps, as measured at a temperature of 25° C. with a Brookfield Synchro-Lectric Viscometer Model D.

The oil-in-water emulsion compositions herein have a low pH. The compositions of the present invention have a pH value of about 3.5 or less, preferably from about 2.5 to about 3.5, more preferably from about 2.8 to about 3.2.

The preferred pH value depends on the particular active or actives employed in the composition of the present invention. For example, for acidic actives of the present invention, the pH of the composition should be carefully chosen so that it is at or below the pKa of the active. By standard definitions, the pKa value for a compound is that pH value at which the material is 50 percent dissociated or ionized to yield its conjugate base and a proton (or hydrated proton). Without being limited by theory, when the pH of the formulation is below the pKa of the active, it is believed that the active will exist primarily in its un-ionized form which should enhance its subsequent deposition onto the skin.

For example, salicylic acid has a reported pKa of 2.97 at 19° C. in aqueous solution. Therefore, it would be useful to formulate salicylic acid containing compositions at or below a pH of about 2.97 in order to suppress ionization and maximize deposition on the skin from the emulsion. See *CRC Handbook of Chemistry and Physics,* 57th Edition, page D-150 (1976).

Even though buffers can be utilized to help maintain the pH of the emulsion compositions, these are not required components, but are merely optional ingredients.

(A) Active Ingredients

The compositions of the present invention comprise a safe and effective amount of an acidic active ingredient, and mixtures thereof, which are preferably soluble in the oil phase of the composition of the present invention and which deposit upon the skin surface.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgement. What is a safe and effective amount of the active ingredient will vary with the specific active, the ability of the active to penetrate through the skin, the age, health condition, and skin condition of the user, and other like factors.

Typically, the actives of the present invention comprise from about 0.05% to about 20%, preferably from about 0.1% to about 10%, and more preferably from about 1% to about 5% by weight of the composition. The actives useful herein preferably have a solubility parameter from about 6 to about 12, preferably from about 7 to about 12, and more preferably from about 9 to about 12. Solubility parameters are well known to the formulation chemist of ordinary skill in the art and are routinely used as a guide for determining compatibilities and solubilities of materials in the formulation process. Without being limited by theory, it is believed that in choosing actives with solubility parameters in the above designated ranges that the actives will tend to be hydrophobic, i.e. lipophilic, and therefore more soluble in the oil phase of the oil-in-water emulsions herein. The lipophilic nature of the active ingredients should help to enhance deposition of the active onto the skin from an oil-in-water emulsion upon rinsing of the emulsion with water. Generally, the preferred actives useful herein with the above outlined solubility parameters will have a solubility in water at 25° C. of less than about 1 gram per about 100 grams of water.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$ = the sum of the heat of vaporization additive group contributions $\sum_i m_i$ = the sum of the molar volume additive group contributions.

Standard tabulations of heat of vaporization and molar volume additive group contributions for a wide variety of atoms and groups of atoms are collected in Barton, A. F. M. *Handbook of Solubility Parameters,* CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science,* vol. 14, no. 2, pp. 147–154 (February 1974), which is incorporated by reference herein in its entirety.

Calculated solubility parameters obey the law of mixtures such that the calculated solubility parameter for a mixture of materials is given by the weighted average of the calculated solubility parameters for each component of that mixture. See, *Handbook of Chemistry and Physics,* 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., *The Chemist's Companion,* John Wiley & Sons, pp. 456–463, (1972), which is incorporated by reference herein in its entirety.

Solubility parameters have also been tabulated for a wide variety of chemical compounds. Tabulations of solubility parameters are found in the *Handbook of Solubility Parameters,* supra.

The actives useful herein can be categorized by their therapeutic benefit or their postulated mode of action. However, it is to be understood that the actives useful herein can in some instances provide more than one therapeutic benefit or operate via more than one mode of action. Therefore, classifications herein are made for the sake of convenience and are not intended to limit the active to that particular application or applications listed. Among the classes of actives useful herein based on therapeutic benefit or mode of action are described in P&G Copending patent application Ser. No. 08/161,104, filed on Dec. 2, 1993, Deckner et al., on pages 10–14, these pages of which are incorporated herein by reference. In addition the following acidic actives which preferably have the above outlined solubility parameters are useful in the compositions of the present invention.

Anti-Acne Actives:

Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atropy Actives:

Examples of antiwrinkle and anti-skin atrophy actives include retinoic acid, salicylic acid, and skin peel agents (e.g., phenol and the like).

Non-Steroidal Anti-Inflammatory Actives (NSAIDS):

Examples of NSAIDS include the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics:

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Tan Accelerators:

Examples of artificial tanning ingredients and tan accelerators include dihydroxyacetone.

Antimicrobial and Antifungal Actives:

Examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

Sunscreening Actives:

Certain sunscreening actives are useful herein. Various sunscreening actives are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al., issued Dec. 17, 1991; and Segarin, et al., at Chapter VIII, pages 189 et seq., of *Cosmetics Science and Technology*, all of which are incorporated herein by reference in their entirety. Several non-limiting examples of sunscreen actives include those selected from the group consisting of p-aminobenzoic acid, 2-phenylbenzimidazole-5-sulfonic acid, and mixtures thereof. Other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety.

The term "salicylic acid" herein includes salicylic acid derivatives, such as 5-octanoyl salicylic acid.

Preferred examples of actives useful herein include those selected from the group consisting of salicylic acid, 3-hydroxy benzoic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, p-aminobenzoic acid, 2-phenylbenzimidazole-5-sulfonic acid, dihydroxyacetone, and mixtures thereof.

More preferred examples of actives useful herein include those selected from the group consisting of salicylic acid, acetyl salicylic acid, cis-retinoic acid, trans-retinoic acid, azelaic acid, tetracycline, ibuprofen, naproxen, acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, and mixtures thereof.

Most preferred examples of actives useful herein include those selected from the group consisting of salicylic acid, cis-retinoic acid, trans-retinoic acid, azelaic acid, resorcinol, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-phenylbenzimidazole-5-sulfonic acid, dihydroxyacetone, and mixtures thereof.

An especially preferred active useful herein is salicylic acid at a level of from about 0.1% to about 5% by weight, preferably from about 1% to about 3% by weight, more preferably from about 1.5% to about 2.5% by weight of the composition.

The above listing of acidic actives also includes salts of these acidic actives as long as these salts remain acidic in the compositions of the present invention.

(B) Alkoxylated Alcohols

The compositions of the present invention comprise from about 0.1% to about 25%, preferably from about 0.1% to about 15%, and more preferably from about 6% to about 10% of an alkoxylated alcohols and/or alkoxylated polyols, which are useful as solubilizing agents for the acidic active ingredients in the oil phase of the oil-in-water emulsions. The alkoxylated alcohols and polyols useful herein generally are hydrophobic, having a solubility in water of less than about 1 gram per about 100 grams of water at 25° C. Preferably, these solvents have a minimum of 10–20 moles of propylene oxide. These compounds are typically formulated into the oil phase of the oil-in-water emulsions as described in the Examples below. Mixtures of alkoxylated alcohols and polyols can be used herein. The alkoxylated alcohols useful herein can be described by the following general formula:

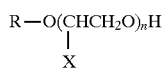

wherein R is selected from the group consisting of alcohols, polyols, diols, and mixtures thereof, having a chainlength of from about 2 to about 18 carbon atoms; n is an integer from about 3 to about 40; X is selected from the group consisting of hydrogen, methyl, ethyl, propyl, and mixtures thereof;

Preferably R is selected from the group consisting of alcohols, polyols, diols, or mixtures thereof, having a chainlength of from about 4 to about 16 carbon atoms; X is methyl; and n is an integer from about 6 to about 35. More preferably R is selected from the group consisting of alcohols, polyols, diols, or mixtures thereof, having a chainlength of from about 4 to about 6 carbon atoms; X is methyl; and n is an integer from about 10 to about 20.

Nonlimiting examples of classes of alkoxylated alcohols useful herein include propoxylated and butoxylated ethers of alcohols and polyols. These compounds can be described as PPG and PBG alkyl ethers wherein the PPG and PBG are commonly used designations for polypropylene glycol and polybutylene glycol, respectively. The average number of PPG or PBG groups in these ethers is commonly given by a number designation after the PPG or PBG. For example, PPG-14 butyl ether, would designate a polypropylene glycol ether of butanol wherein the molecule has on average 14 propylene glycol units.

Nonlimiting examples of alkoxylated alcohols useful herein include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2, 6-hexanetriol ether, and mixtures thereof.

Preferred alkoxylated alcohols are those selected from the group consisting of PPG-14 butyl ether, PPG-15 stearyl ether, PPG-11 stearyl ether, PPG-20 oleyl ether, and mixtures thereof.

More preferred alkoxylated alcohols are those selected from the group consisting of PPG-14 butyl ether, PPG-15 stearyl ether, and mixtures thereof. PPG-14 butyl ether is available under the tradename Fluid AP from Union Carbide Corporation. PPG 15 stearyl ether is available under the tradename Arlamol E from ICI Americas Corporation.

Nonlimiting examples of alkoxylated polyols useful herein include those selected from the group consisting of PPG-10 1,4-butanediol, PPG-12 1,4-butanediol, PPG-14 1,4-butanediol, PPG-2 butanediol, PPG-10 1,6-hexanediol, PPG-12 1,6-hexanediol, PPG-14 hexanediol, PPG-20 hexanediol, and mixtures thereof. Preferred are those selected from the group consisting of PPG-10 1,4-butanediol, PPG-12 1,4-butanediol, PPG-10 1,6-hexanediol, and PPG-12 hexanediol, and mixtures thereof. More preferred is PPG-10 1,4-butanediol. This compound is commercially available under the tradename Macol 57 from PPG/Mazer Corporation.

(C) Acid Stable, Hydrophobic, Structuring Agent

The present invention also comprises from about 1% to about 20%, preferably from about 1% to about 10%, more preferably from about 3% to about 9%, of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C. These structuring agents are useful to assist in the formation of the rheological characteristic of the composition which contribute to the hydrolytic stability of the composition of the present invention. In particular structuring agents assist in the formation of the liquid crystalline gel network structures.

The preferred structuring agents of the present invention are selected from the group consisting of stearyl alcohol, cetyl alcohol, polyethylene glycol ether of stearyl alcohol having an average of about 1 to about 5 ethylene oxide units, polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, polyethylene glycol ether of stearyl alcohol having an average of about 2 ethylene oxide units (steareth-2), polyethylene glycol ether of cetyl alcohol having an average of about 2 ethylene oxide units, and mixtures thereof. Most preferred structuring agents are selected from the group consisting of stearyl alcohol, cetyl alcohol, steareth-2, and mixtures thereof. Most preferred is steareth-2, available under the tradename of Brij® 72 from ICI Americas.

(D) Acid Stable, Hydrophilic Surfactant

The compositions of the present invention comprise from about 0.05% to about 10%, preferably from about 1% to about 6%, and more preferably from about 1% to about 3% of at least one acid stable, hydrophilic surfactant which can disperse the hydrophobic materials in the water phase. The surfactant, at a minimum, must be hydrophilic enough to disperse in water. The surfactant is used herein for emulsifying the oil and water phase ingredients and for stabilizing the resulting emulsion.

The surfactants useful herein can include any of a wide variety of nonionic, cationic, anionic, and zwitterionic surfactants disclosed in prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

The exact emulsifier chosen will depend upon the pH of the composition and the other components present. Suitable surfactants types include tetra-alkyl ammonium salts, ethoxylated alcohols, fatty acid amides, and mixtures thereof.

Preferred herein are cationic emulsifiers, especially dialkyl quaternary ammonium compounds. A wide variety of cationic surfactants useful herein are disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983;; U.S. Pat. No. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's, Detergents & Emulsifiers,* (North American edition 1979) M.C. Publishing Co.; and Schwartz, et al., *Surface Active Agents, Their Chemistry and Technology,* New York: Interscience Publishers, 1949; all of these documents being incorporated herein by reference in their entirety. The cationic surfactants useful herein include cationic ammonium salts such as those having the formula:

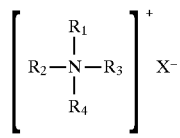

wherein $R_1$, is an alkyl group having from about 12 to about 30 carbon atoms, or an aromatic, aryl or alkaryl groups having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CO-(CH_2)n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of alkyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of dilauryl dimethyl ammonium chloride, distearyl dimethyl ammonium chloride, dimyristyl dimethyl ammonium chloride, dipalmityl dimethyl ammonium chloride, and mixtures thereof.

Also, preferred for use herein are certain nonionic surfactants, especially when used in combination with the cationic emulsifiers described above. It has been found that a blend of a high HLB nonionic surfactant with a low HLB nonionic surfactant is especially preferred. Without being limited by theory, it is believed that this combination of both high and low HLB nonionic surfactants provides compositions demonstrating enhanced emulsion stability. The abbreviation "HLB" stands for hydrophilic lipophilic balance.

The HLB system is well known in the art and is described in detail in "The HLB System, A Time-Saving Guide to Emulsifier Selection", ICI Americas Inc., August 1984, which is incorporated herein by reference.

As defined herein the high HLB nonionic surfactants include any of the well-known nonionic surfactants that have an HLB of from at least about 6 to about 18, preferably from about 8 to about 18, and more preferably from about 10 to about 18. These high HLB nonionic surfactants do not include those emulsifiers with HLB values less than 6, as described below. Typical of these high HLB nonionic emulsifiers are ethoxylated or propoxylated, preferably ethoxylated, alcohols and alkyl phenols, with the alcohol derivatives being preferred. These alcohol derivatives contain a straight or branched chain alkyl group in the $C_{8-30}$, preferably $C_{10-22}$, more preferably $C_{12-20}$, range and generally contain from about 6 to about 30, preferably from about 6 to about 25, ethylene oxide or propylene oxide groups. Among these ethoxylated and propoxylated alcohols, the ethoxylated derivatives are most preferred. Preferred for use herein are polyethylene oxide ethers derived from lauryl alcohol, cetyl alcohol, oleyl alcohol, stearyl alcohol, isostearyl alcohol, myristyl alcohol, behenyl alcohol, and mixtures thereof. More preferred for use herein are: polyoxyethylene 10 cetyl ether, known by the CTFA designation as ceteth-10; polyoxyethylene (21) stearyl ether, known by the CTFA designation steareth-21; coconut alkyl polyethoxylate (6.5); decyl polyethoxylate (6); and mixtures thereof. Most preferred for use herein are ceteth-10, steareth-21, and mixtures thereof.

Detailed listings of high HLB nonionic emulsifiers can be found in McCutcheon's EMULSIFIERS AND DETERGENTS, North American Edition, 1984, McCutcheon Division, MC Publishing Company, which has already been incorporated herein by reference.

The low HLB nonionic surfactants are defined herein as any of the well known nonionic surfactants having an HLB value from about 1 to less than about 6. These low HLB nonionic surfactants do not include the high HLB nonionic surfactant described above.

Examples of these low HLB nonionic emulsifiers are ethoxylated alcohols wherein these alcohol derivatives contain a straight or branched chain alkyl group in the $C_{8-30}$, preferably $C_{10-22}$, more preferably $C_{12-20}$, range, and generally contain from about 1 to about 5 ethylene oxide groups per molecule.

Some nonlimiting examples of these low HLB nonionic emulsifiers useful herein include lauryl alcohol ethoxylated with 1 mole of ethylene oxide (i.e. laureth-1), laureth-2, laureth-3, laureth-4, laureth-5, and mixtures thereof.

Detailed listings of low HLB emulsifiers can be found in McCutcheon's EMULSIFIERS AND DETERGENTS, North American Edition, 1984, McCutcheon Division, MC Publishing Company, which has already been incorporated herein by reference.

In the present invention, it has been found that when a combination of a high and a low HLB nonionic emulsifer are used together, that the combination of steareth-21 and/or ceteth-10 with steareth-2 is preferred.

(E) Water

The compositions of the present invention comprise from about 25% to about 99.7%, more preferably from about 65% to about 95%, and most preferably from about 70% to about 90% water.

Optional Components

Each of the water and oil phases of the emulsions can comprise a wide variety of optional components. Typical of such optional components are:

Polypropylene Glycols

Polypropylene glycols and propylene glycol are useful herein, at a level of from about 1% to about 5% by weight of the composition, preferably from about 2% to about 3.5% by weight of the composition, to enhance the penetration of the acidic active ingredient of the present invention. Polypropylene glycols are polymers which are typically formed from the polymerization of propylene oxide, propylene glycol, propylchlorohydrin, propylbromohydrin, and other related materials. Polypropylene glycols are represented by the following formula:

wherein n is an integer from about 10 to about 50, preferably from about 15 to about 40, and more preferably from about 20 to about 34. In the above structure, even though one isomeric orientation is depicted for convenience, this depiction is not intended to preclude other isomeric structures. The polypropylene glycols are commonly designated as PPG's followed by a number indicating the average number of repeating units in the structure. For example, PPG-30 would correspond to the above structure wherein n has an average value of about 30. Based on this nomenclature, the polypropylene glycols useful herein encompass those designated as PPG-10 through PPG-50, more preferably those designated as PPG-15 through PPG-40, and most preferably those designated as PPG-20 through PPG-34.

Humectants

Another optional component of the compositions of the present invention is a humectant. When used herein, the humectant can comprise from about 0.1% to about 20%, more preferably from about 0.5% to about 10%, and most preferably from about 1% to about 5% by weight of the composition. Even though these materials are defined herein as humectants, they can also possess moisturizing, skin conditioning, and other related properties.

Examples of humectants useful herein include materials such as urea; guanidine; saturated or unsaturated alkyl alpha hydroxy acids such as glycolic acid and glycolate salts (e.g. ammonium and quaternary alkyl ammonium) and lactic acid and lactate salts (e.g. ammonium and quaternary alkyl ammonium); aloe vera in any of its variety of forms (e.g. aloe vera gel); polyhydroxy alcohols such as sorbitol, glycerol, low molecular weight polypropylene glycols (e.g., dipropylene glycol and tripropylene glycol), hexanetriol, propylene glycol, butylene glycol, hexylene glycol, and the like; polyethylene glycol; sugars and starches; sugar and starch derivatives (e.g., alkoxylated glucose); hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; propoxylated glycerol (as described in U.S. Pat. No. 4,976,953 to Orr et al., issued Dec. 11, 1990, which is incorporated by reference herein in its entirety); and mixtures thereof.

Preferred humectants useful in the compositions of the present invention are urea, C3–C6 diols and triols, low molecular weight polypropylene glycols, and propoxylated glycerin. Preferred humectants include those materials selected from the group consisting of urea, propylene glycol, 1,3-dihydroxypropane, glycerin, butylene glycol, hexylene glycol, 1,4-dihydroxyhexane, 1,2,6-hexanetriol, dipropylene glycol, tripropylene glycol, and mixtures thereof. More preferred are those selected from the group consisting of urea, glycerin, propylene glycol, hexylene glycol, glycerin, dipropylene glycol, tripropylene glycol, and mixtures thereof. Most preferred is propylene glycol, urea, glycerin, and mixtures thereof.

Emollients

The compositions of the present invention can also include an emollient. Examples of suitable emollients include, but are not limited to, volatile and non-volatile silicone oils (e.g., dimethicone, cyclomethicone, dimethiconol, and the like), highly branched hydrocarbons, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 0.1% to about 25%, more preferably from about 0.5% to about 10%, and most preferably from about 0.5% to about 5% by weight of the composition.

Additional Ingredients

A variety of additional ingredients can be incorporated into the compositions of the present invention. These additional ingredients, at a minimum, must be acid stable. Non-limiting examples of these additional ingredients include vitamins and derivatives thereof (e.g. tocopherol, panthenol, and the like); other thickening agents (e.g., polyacrylamide and $C_{13-14}$ isoparaffin and laureth-7, available as Sepigel 305 from Seppic Corp., Fairfield, N.J.; and branched polysaccharides such as scleroglucan available under the tradename Clearogel® CS 11 from Michel Mercier Products Inc., Mountainside, N.J.); saturated and/or unsaturated alkyl alpha hydroxy acids; resins; gums (e.g. guar gum, xanthan gum and the like); waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220®); abrasive scrub particles for cleansing and exfoliating the skin [e.g., ACuscrub® Mild Abrasives (e.g., ACuscrub® 30, 31, 32, 40, 41, 42, 43, 44, 50, 51, and 52) available from Allied Signal, Inc., Morristown, N.J.; and 3M Brand PMU Capsules microencapsulated mineral oil available from 3M Corporation, St. Paul, Minn.]; preservatives for maintaining the antimicrobial integrity of the compositions; skin penetration aids such as DMSO, 1-dodecylazacycloheptan-2-one (available as Azone® from the Upjohn Co.) and the like; artificial tanning ingredients and tan accelerators such as tyrosine, tyrosine esters such as ethyl tyrosinate, and phospho-DOPA); skin bleaching (or lightening) agents including but not limited to hydroquinone, kojic acid and sodium metabisulfite; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

Preferred ingredients are saturated and/or unsaturated alkyl alpha hydroxy acids, at a level of from about 0.05% to about 5% by weight of the composition, such as lactic acid, lactate salts (e.g. ammonium and quaternary alkyl ammonium), glycolic acid, glycolate salts (e.g. ammonium and quaternary alkyl ammonium), and fruit acids. A discussion of alpha hydroxy acids is disclosed in Walter P. Smith, Hydroxy Acids and Skin Aging, *Soap/Cosmetics/Chemical Specialties*, pp. 54–59, (September 1993), which is herein incorporated by reference in its entirety.

Methods for Desquamation

The present invention also relates to methods wherein an effective amount of an acidic active ingredient is deposited on the skin in order to modify the condition being treated or to deliver the desired benefit. An effective amount is an adequate amount to deliver the desired benefit but low enough to avoid serious side effects at a reasonable benefit to risk ratio within the scope of sound medical judgement. What is a safe and effective amount of the acidic active will vary with the specific active, the ability of the active to penetrate through the skin, the age of the user, the health condition of the user, and the skin condition of the user, and other like factors. Such methods comprise topically applying to the skin or scalp, an effective amount of the composition of the present invention. For example, an effective amount of a composition containing salicylic acid means an amount sufficient to provide a scale removal benefit, generally from about 0.004 mg/cm$^2$ to about 0.1 mg/cm$^2$, more preferably from about 0.02 mg/cm$^2$ to about 0.06 mg/cm$^2$, and even more preferably about 0.04 mg/cm$^2$. The composition can be applied for several days in a row, weeks, months or years at an appropriate interval. Appropriate intervals are from about three times daily to about one time every three days, preferably from about two times daily to about one time every other day, more preferably about one time daily, until satisfactory desquamation, moisturization, and hydration are achieved.

EXAMPLES

The following examples further describe and demonstrate embodiments within the scope of the present invention. The examples are given solely for the purpose of illustration and are not to be construed as limitations of the present invention, as many variations thereof are possible Without departing from the spirit and scope of the invention.

Ingredients are identified by chemical or CTFA name.

Examples I–II

Leave On Moisturizing Products Containing Salicylic Acid

A leave on moisturizing, oil-in-water emulsion containing salicylic acid is prepared by combining the following ingredients using conventional mixing techniques as described below.

| Ingredient | I WT. % | II WT. % |
|---|---|---|
| Salicylic Acid | 2 | 1.5 |
| PPG-14 Butyl Ether | 8.00 | 8.00 |
| Glycerin | 4.00 | 4.00 |
| Stearyl Alcohol | 1.5 | 1.5 |
| Cetyl Alcohol | 3.00 | 3.00 |
| Distearyl Dimethyl Ammonium Chloride | 0.1 | 0.1 |
| Propylene Glycol | 3.00 | 3.00 |
| Steareth-21[1] | 2.0 | 2.0 |
| Steareth-2[2] | 1.0 | 1.0 |
| Dimethicone[3] | 1.0 | 1.0 |
| Cyclomethicone[4] | 1.0 | 1.0 |
| Disodium EDTA | 0.02 | 0.02 |
| Minors | 0.07 | 0.07 |
| Water | QS 100 | QS 100 |

[1]Polyethylene glycol ether of stearyl alcohol with an average of about 21 moles of ethylene oxide.
[2]Polyethylene glycol ether of stearyl alcohol with an average of about 2 moles of ethylene oxide.
[3]A mixture of fully methylated linear siloxane polymers end blocked with trimethyldiloxy units.
[4]A cyclic dimethyl polysiloxane compound.

The above compositions are prepared as follows:

First prepare a water phase by heating the water to a temperature of about 180° F. (82° C.) and adding the distearyl dimethyl ammonium chloride, glycerin, and propylene glycol. Keep this mixture at a temperature of from about 65° C. to about 75° C.

In a separate vessel prepare the oil phase by mixing the cetyl alcohol, stearyl alcohol, steareth-2, steareth-21, the dimethicone, and the cyclomethicone and heating the mixture to a temperature of from about 65° C. to about 75° C.

In a separate vessel prepare the salicylic acid phase by mixing the salicylic acid into the PPG-14 butyl ether at a temperature of from about 65° C. to about 75° C.

Thereafter, mix the salicylic acid phase into the oil phase at a temperature of from about 65° C. to about 75° C. Add the oil phase mixture to the water phase mixture and mill at a temperature of from about 65° C. to about 75° C. Cool the resulting mixture to a temperature of from about 40° C. to about 50° C. Thereafter, add a mixture comprising the minor ingredients and the disodium EDTA to the emulsion. Cool to ambient temperature. In the alternative the above compositions can be prepared as follows:

First prepare a water phase by heating the water to a temperature of about 180° F. (82° C.) and adding the distearyl dimethyl ammonium chloride, glycerin, propylene glycol, cetyl alcohol, stearyl alcohol, steareth-2, and steareth-21. Keep this mixture at a temperature of from about 65° C. to about 75° C.

In a separate vessel prepare the salicylic acid phase by mixing the salicylic acid, PPG-14 butyl ether, the dimethicone, and the cyclomethicone at a temperature of from about 65° C. to about 75° C.

Thereafter, mix the salicylic acid phase mixture into the water phase mixture and mill at a temperature of from about 65° C. to about 75° C. Cool the resulting mixture to a temperature of from about 40° C. to about 50° C. Thereafter, add a mixture comprising the minor ingredients and the disodium EDTA to the emulsion. Cool to ambient temperature.

The resulting compositions are useful for application to the skin for delivering salicylic acid and are useful for treating wrinkles, dry skin and other age-related conditions of the skin.

What is claimed is:

1. A skin care composition, comprising:
   (A) from about 0.05% to about 20% of an acidic active ingredient having a solubility parameter of from about 6 to about 12, wherein the acidic active is selected from the group consisting of salicylic acid, acetyl salicylic acid, cis-retinoic acid, trans-retinoic acid, azelaic acid, tetracycline, ibuprofen, naproxen, acetominophen, hydrocortisone, resorcinol, phenoxyethanol, phenoxypropanol, pbenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, and mixtures thereof;
   (B) from about 0.1% to about 25% of a hydrophobic alkoxylated alcohol of the formula:

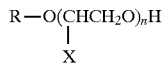

wherein R is an alcohol having a chain length of from about 2 to about 18 carbon atoms; n is an integer from about 3 to about 40; and X is selected from the group consisting of methyl, ethyl, propyl and mixtures thereof,
   (C) from about 1% to about 20% of an acid stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;
   (D) from about 0.05% to about 10% of an acid stable, hydrophilic emulsifying surfactant mixture comprising a cationic surfactant, a high HLB nonionic surfactant having an HLB of at least about 6 to about 18 selected from the group consisting of ethoxylated alcohols derived from straight or branched chain $C_8$–$C_{30}$ alkyl groups and having from about 6 to about 30 ethylene oxide groups and ethoxylated alkyl phenols, and a low HLB nonionic surfactant having an HLB of from about 1 to less than about 6 selected from the group consisting of ethoxylated alcohols derived from straight or branched chain $C_8$–$C_{30}$ alkyl groups and having, from about 1 to about 5 ethylene oxide groups; and
   (E) from about 25% to about 99.7% water;
wherein the pH of the composition is about 3.5 or less and the composition is in the form of a leave on skin care composition.

2. The composition of claim 1 wherein the pH is from about 2.5 to about 3.5.

3. The composition of claim 2 wherein the pH is from about 2.8 to about 3.2.

4. The composition of claim 1 wherein the level of acidic active is from about 0.1% to about 10% by weight of the composition.

5. The composition of claim 4 wherein the hydrophobic structuring agent is selected from the group consisting of stearyl alcohol, cetyl alcohol, polyethylene glycol ether of stearyl alcohol having an average of about 2 ethylene oxide units, and mixtures thereof.

6. The composition of claim 4 wherein the ratio of component (C) to component (D) is from about 20:1 to about 1:1.

7. The composition of claim 6 wherein the ratio of component (C) to component (D) is from about 10:1 to about 1:1.

8. The composition of claim 7 wherein the ratio of component (C) to component (D) is from about 5:1 to about 1:1.

9. The composition of claim 1 wherein the surfactant is a cationic surfactant having the formula:

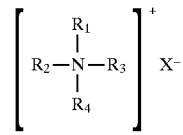

wherein $R_1$, is an alkyl group having from about 12 to about 30 carbon atoms, or an aromatic, aryl or alkaryl groups having from about 12 to about 30 carbon atoms; $R_2$, $R_3$, and $R_4$ are independently selected from hydrogen, an alkyl group having from about 1 to about 22 carbon atoms, or an aromatic, aryl or alkaryl groups having from about 12 to about 22 carbon atoms; and X is any compatible anion.

10. The composition of claim 9 wherein the cationic surfactant is selected from the group consisting of dilauryl dimethyl ammonium chloride, distearyl dimethyl ammonium chloride, dimyristyl dimethyl ammonium chloride, dipalmityl dimethyl ammonium chloride, and mixtures thereof.

11. The composition of claim 10 wherein the high HLB nonionic surfactant is selected from the group consisting of coconut alkyl polyethoxylate (6.5), decyl polyethoxylate (6), polyoxyethylene (10) cetyl ether, polyoxyethylene (21) stearyl ether, and mixtures thereof.

12. The composition of claim 11 wherein the high HLB nonionic surfactant is selected from the group consisting of polyoxyethylene (10) cetyl ether, polyoxyethylene (21) stearyl ether, and mixtures thereof.

13. The composition of claim 1 wherein the acidic active has a solubility parameter from about 9 to about 12.

14. The composition of claim 13 wherein the acidic active is selected from the group consisting of salicylic acid, salicylic acid derivative, cis-retinoic acid, trans-retinoic acid, azelaic acid, ibuprofen, naproxen, 2-phenylbenzimidazole-5-sulfonic acid, and mixtures thereof.

15. The composition of claim 14 wherein the alkoxylated alcohols are selected from the group consisting of PPG-14 butyl ether, PPG-15 stearyl ether, PPG-11 stearyl ether, PPG-20 oleyl ether, PPG-10 1,4-butanediol, PPG-12 1,4-butanediol, PPG-10 1,6-hexanediol, and PPG-12 hexanediol, and mixtures thereof.

16. The composition of claim 15 wherein the alkoxylated alcohols are selected from the group consisting of PPG-14 butyl ether, PPG-15 stearyl ether, PPG-10 1,4-butanediol, and mixtures thereof.

17. The composition of claim 16 wherein the acidic active is salicylic acid at a level of from about 0.1% to about 5% by weight of the composition.

18. The composition of claim 17 wherein the composition additionally comprises from about 1% to about 5% by weight of the composition of propylene glycol.

19. The composition of claim 18 wherein the level of propylene glycol is from about 2% to about 3.5% by weight of the composition.

20. The composition of claim 14 wherein the hydrophobic structuring agent is selected from the group consisting of stearyl alcohol, cetyl alcohol, polyethylene glycol ether of stearyl alcohol having an average of about 2 ethylene oxide units, and mixtures thereof.

21. The composition of claim 14 wherein the ratio of component (C) to component (D) is from about 20:1 to about 1:1.

22. The composition of claim 21 wherein the ratio of component (C) to component (D) is from about 10:1 to about 1:1.

23. The composition of claim 22 wherein the ratio of component (C) to component (D) is from about 5:1 to about 1:1.

24. The composition of claim 1 wherein the viscosity of the composition is from about 3,000 to about 200,000 cps.

* * * * *

UNITED STATES PATENT AND TRADEMARK OFFICE
CERTIFICATE OF CORRECTION

PATENT NO.    : 5,824,666
DATED         : October 20, 1998
INVENTOR(S)   : George E. Deckner et al.

It is certified that error appears in the above-identified patent and that said Letters Patent is hereby corrected as shown below:

At column 11, line 51 "$R_5CO-(CH_2)n-$" should read --$R_5CO-(CH_2)_n-$--.

At column 16, line 30 "Without" should read --without--.

At column 17, line 49 "pbenoxyisopropanol" should read --phenoxyisopropanol--.

Signed and Sealed this

Twentieth Day of April, 1999

Attest:

Q. TODD DICKINSON

*Attesting Officer*     *Acting Commissioner of Patents and Trademarks*